United States Patent [19]

DeQuattro et al.

[11] Patent Number: 4,591,551
[45] Date of Patent: May 27, 1986

[54] RADIOENZYMATIC METHOD FOR ASSAYING NORMETANEPHRINE AND OCTOPAMINE

[75] Inventors: Vincent DeQuattro, Pasadena, Calif.; Kiyoshi Kobayashi, Sendai, Japan

[73] Assignee: University of Southern California, Los Angeles, Calif.

[21] Appl. No.: 612,840

[22] Filed: May 22, 1984

Related U.S. Application Data

[63] Continuation of Ser. No. 282,464, Jul. 13, 1981, which is a continuation-in-part of Ser. No. 122,623, Feb. 19, 1980.

[51] Int. Cl.$^4$ ............................ C12Q 1/48; C12N 9/10
[52] U.S. Cl. ........................................ 435/15; 435/193
[58] Field of Search ............... 436/504, 542, 543, 544; 435/15, 193

[56] References Cited

U.S. PATENT DOCUMENTS

| | | | |
|---|---|---|---|
| 4,041,076 | 8/1977 | Avenia et al. | 23/230 B |
| 4,108,973 | 8/1978 | Avenia et al. | 424/1 |
| 4,242,456 | 12/1980 | Johnson et al. | 435/15 |
| 4,275,150 | 6/1981 | Vlachakis | 424/1.1 |

OTHER PUBLICATIONS

Kobayashi et al., Clinica Chimica Acta, 107 (1980) 163–73.
Ben-Jonathan et al., Endocrinol., 98 (1976) 1497–1507.
Rossi-Fanelli et al., II Al. J. Biochem., 27 (1978) 450–65.
Dzigdzic et al., Fed. Proc., 37 (1978) 510.
Hoertnagl et al., Chem. Abstracts, 87 (1977) #180207a.
Nagel-Hiemke et al., Chem. Abstracts, 95 (1981) #146428d.

*Primary Examiner*—Christine M. Nucker
*Attorney, Agent, or Firm*—Nilsson, Robbins, Dalgarn, Berliner, Carson & Wurst

[57] ABSTRACT

An improvement in the method for assaying normetanephrine and octopamine. A procedure is used in which the phenylethanolamine in a sample is enzymatically transmethylated in an incubation mixture of the phenylethanolamine, a compound containing a transferable tritiated methyl group and a transfer enzyme, to form a tritiated N-methyl derivative, and the radioactivity of the derivative is measured. In accordance with the present improvement, incubation of the mixture is conducted at a pH of at least 8.6, preferably in the range of 8.8–9.3. Prior to incubation, as appropriate, the sample may be deproteinized and the phenylethanolamine concentrated.

12 Claims, 2 Drawing Figures

RADIOENZYMATIC METHOD FOR ASSAYING NORMETANEPHRINE AND OCTOPAMINE

CROSS REFERENCE TO RELATED APPLICATION

This is a continuation of application Ser. No. 282,464, filed July 13, 1981 which is a continuation-in-part of our application Ser. No. 122,623 filed Feb. 19, 1980.

FIELD OF THE INVENTION

The field of art to which the invention pertains includes the field of phenylethanolamine assay.

BACKGROUND AND SUMMARY OF THE INVENTION

For a variety of clinical reasons it is desirable to quantitatively assay one or more phenylethanolamines found in plasma or in urine. For example, the diagnosis of pheochromocytoma has been based upon measurement of the increased excretion of norepinephrine and its metabolite normetanephrine. Such diagnosis is important because these tumors produce a potentially curable form of hypertension, which otherwise is fatal. Also, norepinephrine is the neurotransmitter released from sympathetic nerve terminals. The determination of normetanephrine metabolite can provide important information regarding sympathetic nerve function and norephinephrine metabolism. Another phenylethanolamine of interest is octopamine, the determination of which may assist in the evaluation of encephalopathy.

Unfortunately, techniques for assaying phenylethanolamines and their metabolites are often nonspecific, laborious, tedious and/or frequently give false positive results. Henry et al in "A Sensitive Radioenzymatic Assay for Norepinephrine in Tissues and Plasma", *Life Sciences*, Vol. 16, p. 375 describe the reaction of a phenylethanolamine with tritiated S-adenosyl-L-methionine promoted by the transfer enzyme phenylethanolamine-N-methyl transferase to form the tritiated N-methyl derivative of the phenylethanolamine. Although the method is applied by Henry et al to normetanephrine in a comparison of substrate specificity, they are not successful in detecting normetanephrine. In a related procedure Molinoff et al in "An Enzymatic Assay for Octopamine and Other β-Hydroxylated Phenylethylamines", *The Journal of Pharmacology and Experimental Therapeutics*, Vol. 170, 1970, No. 2, P. 253 react octopamine with S-adenosyl-L-methionine made radioactive with $C^{14}$, also using phenylethanolamine-N-methyl transferase to initiate the transmethylation. Molinoff et al also apply the procedure to normetanephrine to determine the specificity of the assay and they too had no success in assaying normetanephrine. These failures to quantitatively determine normetanephrine have been the subject of speculation. It has been hypothesized that both urine and serum contain an unidentified inhibitor for the phenylethanolamine-N-methyl transferase. See in this regard Manghani et al in "Urinary and Serum Octopamine in Patients with Portal-Systemic Encephalopathy", The Lancet, Nov. 15, 1975, p. 943. Manghani et al describe a method similar to that of Molinoff et al in assaying octopamine in urine. They ascribe poor recovery in undiluted samples to the presence of a phenylethanolamine-N-methyl transferase inhibitor. Some degree of success in determining urinary normetanephrine was achieved by Vlachakis and DeQuattro in "A Simple and Specific Radioenzymatic Assay for Measurement of Urinary Normetanephrine", *Biochemical Medicine*, 20, pp. 107–114 (1978). However, even here the results are not as satisfactory as desired, there still being too much inhibition.

The present disclosure described a rapid, specific and inexpensive assaying method for the quantitative measurement of two specific phenylethanolamines: normetanephrine and octopamine. The method has particular importance with respect to the detection of normetanephrine in hypertensive patients even during therapy, as no anti-hypertensive drugs interfere with the assay. Furthermore, the method can be conducted without the need for preservatives and with samples, such as blood, collected under less stringent conditions of temperature than that required for the assaying of other phenylethanolamine such as norepinephrine; these advantages arise from the general high stability of normetanephrine and octopamine.

More specifically, a method is provided which is an improvement upon the prior art method of converting normetanephrine to metanephrine as exemplified by the Vlachakis and DeQuattro method, supra, utilizing techniques from the Henry et al method, supra and also from the method of Peuler and Johnson, "Simultaneous Single Isotope Radioenzymatic Assay of Plasma Norepinephrine, Epinephrine and Dopamine", *Life Sciences*, Vol. 21, p. 625 (1977). In the Peuler and Johnson method, one of the hydrogen atoms of the amine substituent of the phenylethanolamine is replaced by a methyl group, supplied by transmethylation with S-adenosyl-L-methionine promoted by the transfer enzyme phenylethanolamine-N-methyl transferase. The transferable methyl group on the S-adenosyl-L-methionine is tritiated, thereby radioactively labeling the produced N-methylated phenylethanolamine. The present invention provides an improvement on that method achieved in its most preferred form by a combination of the following steps and conditions: (a) whereas the prior art conducts the transmethylation incubation at a pH of about 6.5 to 8.2, in the present invention transmethylation incubation of the mixture is conducted at a pH of at least 8.6, preferably in the range of 8.8–9.3; (b) when the sample is plasma or brain tissue or other substance containing a high level of protein, prior to incubation, the sample is deproteinized; and (c) prior to incubation, the phenylethanolamine in the sample may be concentrated.

The above conditions and steps significantly decrease enzymatic inhibition and sufficiently increase sensitivity of the assay to determine plasma levels of normetanephrine. Octopamine can be determined without the deproteinization and concentration steps but by combining all three steps and conditions, one obtains a greater degree of reliability in the determination of octopamine.

In particular embodiments, the incubation mixture comprises a combination of ethylene diamine tetraacetic acid (EDTA) and a mixture of tris(hydroxymethyl)amino methane and its hydrochloric salt (the mixture being referred to hereinafter as tris) at a molar ratio sufficient to yield the desired pH. For example, by using 25 millimoles of EDTA per mole of tris, a pH of 10.3 is obtained. Deproteinization can be accomplished by reacting protein in the sample with trichloracetic acid and separating the reaction product from the sample. The normetanephrine or octopamine can be purified by weak cation exchange, e.g. conducted by chromatographic extraction through weak cation exchange resin.

The techniques presented by this disclosure are very convenient both to the patient and to laboratory personnel. For example, urine or plasma can be collected in any clean container without any preservative and an aliquot can be stored in a freezer until analysis. The assay procedure allows collection of a random sample when the patient is hypertensive or symptomatic; analysis can be conducted even several days later. The assay is sensitive enough to be used as a routine test. For example, one can measure as little as 30 picograms per milliliter of normetanephrine, thus providing a specific, rapid and accurate assay for the detection of pheochromocytoma.

DETAILED DESCRIPTION

Figure 1:
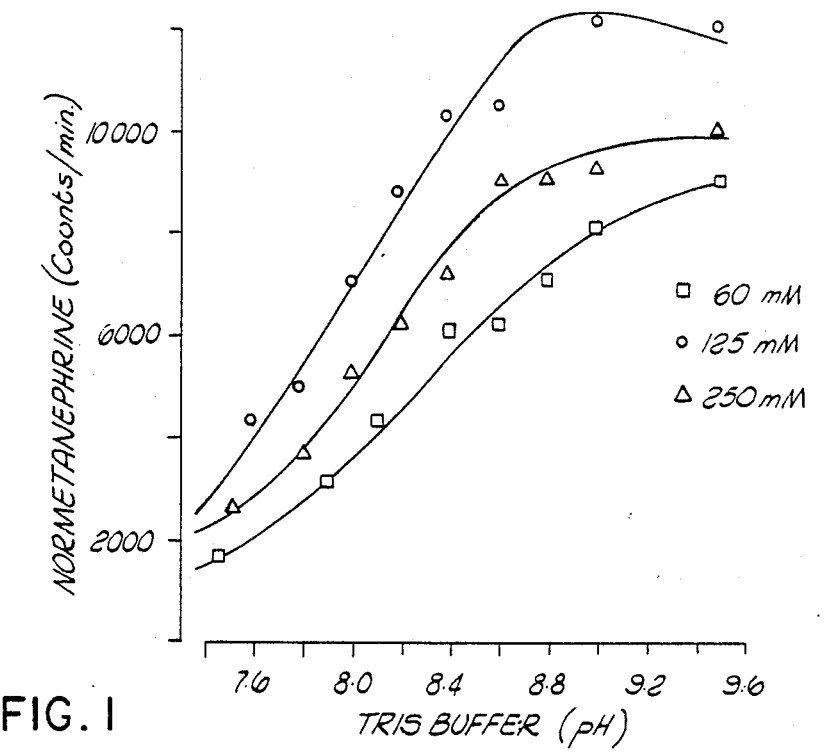
FIG. 1 is a plot of normetanephrine detected versus the pH of tris buffer incubation mixture at three concentration levels.

The following description and examples will relate primarily to the assaying of normetanephrine; but the techniques are directly applicable to the assaying of octopamine. The sample can be any material in which is naturally found the excreted target normetanephrine or octopamine, such as urine, plasma, brain tissue, etc. As above indicated, prior to the usual incubation step, as appropriate to the sample, for example plasma, the sample can be subject to deproteinization and extraction, for concentration, of the target phenylethanolamine. For deproteinization, one could use any organic acid which will react with the sample protein to form a precipitate but which will not react with the target phenylethanolamine. Such an acid is exemplified by trichloroacetic acid; other organic acids that can be used include perchloric acid and tricarboxylic acid. The deproteinized sample can be separated from the precipitate by centrifugation and transfer of the supernatant, following which the target phenylethanolamine is concentrated. This can be accomplished by any technique which will tend to isolate the target phenylethanolamine from other phenylethanolamines and from other components of the sample. A convenient technique to concentrate the target phenylethanolamine is by weak cation exchange conducted by chromatographic extraction through a weak cation exchange resin. In this regard, one can use the deproteinization and Dowex 50 chromatography technique described by Nagatsu and Udenfriend, "Photometric Assay of Dopamine-$\beta$-Hydroxylase Activity in Human Blood", *Clinical Chemistry*, 18. p. 989-983 (1972). The Dowex column in this technique uses a sulfonic acid type ion exchange resin AG50WCU, 200-400 mesh, hydrogen type, 100200 U.S. standard, Bio. Rad. #142-1351.

Following deproteinization, where appropriate, and concentration, transmethylation is accomplished using known methods, for example, using the method of Henry et al, supra. In this method, transmethylation is accomplished using commercially available tritiated S-adenosyl-L-methionine, having one or more hydrogen atoms on its methyl group substituted with tritium ($^3$H), promoted by a transfer enzyme therefor. Such a transfer enzyme is phenylethanolamine-N-methyl-transferase obtainable from the medullary tissue of bovine adrenals, as known to the art. However, in accordance with the present invention, the incubation mixture is buffered to a pH of at least 8.6, in contrast to a range of 6.2 to 8.2 used in the technique described in the literature.

An internal standard consisting of a known amount of the target phenylethanolamine can be added to a duplicate sample for concurrent processing made up of the reagents alone without the sample and without the standard. The reaction mixture can be incubated for a time sufficient to assure the completion of reaction, or it can be terminated after a specific length of time by cooling in an ice bath and raising the pH to a level above that which is suitable for transmethylation (e.g., to a pH of 11.0).

The resultant mixture can be subjected to thin film chromotography using known techniques, such as that of Peuler and Johnson, supra, in which an automatic thin layer chromotography multispotter is used to spot the mixture on silica gel plates. The plates can be developed and dried, and bands corresponding to the N-methylated target phenylethanolamine can be located by inspection, for example under short wave ultraviolet light. The target band can be scraped into scintillation vials containing ammonium hydroxide to which scintillation fluid is added. Thereafter, the vials can be placed into a liquid scintillation counter and the counts per minute determined.

The present procedure does not result in 100% recovery of the N-methylated phenylethanolamine. However, the procedure has a sufficiently high degree of precision so that one can use a predetermined recovery rate to accurately calculate the quantity of target phenylethanolamine in the sample. For example, it has been found that the overall mean recovery for the entire assay calculated when 1 ng of normetanephrine is added to cooled plasma is 70.0+2.8%. Accordingly, the amount of target phenylethanolamine, as the tritiated N-methylated phenylethanolamine in picograms per milliliter of sample, can be determined using the following formula:

$$\frac{CPM_{sample} - CPM_{blank}}{CPM_{(sample+standard)} - CPM_{sample}} \times$$

$$100 \text{ pg} \times \frac{200}{\text{aliquot size}} \times \frac{100}{\text{recovery rate, \%}}$$

One can determine the counts per minute (CPM) of the sample, the blank, and the sample plus internal standard, and applying the above formula, one can obtain in picograms the amount of N-methylated phenylethanolamine per milliliter of sample.

The following examples will serve to further illustrate the invention.

EXAMPLE I

Plasma

Preparation of Phenylethanolamine-N-Methyl-Transferase (PNMT)

PNMT was partially purified from bovine adrenal medulla according to the method of Henry et al, supra. In accordance with that procedure, thirty-three grams of medullary tissue are dissected from 15 fresh bovine adrenals and homogenized in 280 ml of 1.19 percent KCl solution. The homogenate is centrifuged at 40,000 g for one hour and the supernatant is filtered and recentrifuged at 100,000 g for one hour. To 250 ml of the supernatant are added 5 ml of 0.05M sodium phosphate buffer, pH 7.5 and 44 gm of solid ammonium sulfate. Another 19.8 gm of ammonium sulfate per 100 ml are added. The supernatant is discarded and the precipitate resuspended in 100 ml of 55 percent saturated ammonium sulfate—0.0125M sodium phosphate. The solution is recentrifuged and for each 100 ml of supernatant, 17 gm of ammonium sulfate are added. After centrifugation, the precipitate is resuspended in 50 ml of 0.005M tris, pH 7.4, containing 0.1 mM dithiothreitol and dialyzed in four liters of the buffer with four changes in a 16 hour period. The dialyzed enzyme is then centrifuged at 40,000 g for 10 minutes and frozen in small aliquots.

In the present procedure, the PNMT is diluted so as to contain 4.7 mg/ml of protein, showing 22.7 pmole/ug protein/hour of enzymatic activity when the activity was determined by Axelrod's method [J. Axelrod, J. Biol. Chem., 237, pp. 1657–1660 (1962)].

Sample Preparation

Blood specimens were collected into commercial vactainer tubes containing 15 milligrams EDTA for 10 ml of blood and placed on ice immediately. After centrifugation at 4° C., exactly 1 ml of plasma was transferred to a 10 ml test tube and kept in the freezer at −20° C. until the assay was performed. In this condition, plasma normetanephrine is stable for at least 2 months.

Pretreatment of Plasma

Deproteinization of plasma and concentration by extration of normetanephrine by cation exchange resin column were performed prior to the enzymatic assay. For deproteinization, 3 ml of 5% trichloracetic acid (TCA) was added to a tube containing 1 ml of stored plasma, and the tube was agitated and centrifuged. The supernatant was transferred to a chromatographic column (size 0.5×10 cm with 10 ml reservoir) packed with 0.5 ml of Dowex 50W ($H^+$, 200–400 mesh). The tube and precipitate were washed with 2 ml of 5% TCA and the washings were also poured into the column. The column was washed with 15 ml of deionized water, and then the adsorbed amines were eluted by 2.3 ml of 4N $NH_4OH$ containing 30% methyl alcohol. The initial 0.3 ml of eluate was discarded and the remaining 2.0 ml was collected. The column eluate was placed on a hot plate (at 52° C.) and evaporated under a nitrogen gas stream. After evaporation, the tube was restored to 200 microliter by 0.001N HCl and kept in the refrigerator overnight for the enzymatic assay.

For each assay run, four tubes of pooled plasma (two pooled plasma and two pooled plasma with 1 ng of the levoform of normetanephrine—which is not transmethylated) were processed along with the specimen from the subject to standardize the methods and to check on overall recovery.

Enzymatic Assay

Duplicate aliquots (20–50 microliters) of the processed specimens were transferred to disposable culture tubes (13×100 mm); 10 ul of deionized water was added to one and the same volume of normetanephrine standard solution (100 pm) was added to the other. Two tubes of 50 microliters of 0.001N NCl were used for blanks instead of plasma for each assay run. The enzymatic reaction was initiated by the addition of a mixture of 10 ul each of 0.5M tris-HCl with 12.5 mM EDTA (pH 10.0), diluted tritiated S-adenosyl-L-ethionine (SAM-$H^3$ at 1.25 microCurie) and phenylethanolamine-N-methyl transferase prepared as above. The pH of the incubation mixture was 9.2. The incubation was carried out for sixty minutes at 37° C. and terminated by cooling in an ice bath and the addition of 100 ul of 0.5M borate buffer (pH 10.0) containing 5 micromole of metanephrine to facilitate the location of chromotography bands.

Radioactive products were extracted into 3 ml of toluene isoamyl-alcohol mixture (3:2) by agitation on a vortex mixer. The organic layer was separated by centrifugation, transferred to another set of tubes after quick freezing of the aqueous layer in a dry ice acetone bath and subsequently washed by 50 microliter of 0.5M borate buffer (pH 10.0) with similar procedures. Then the organic layer was transferred to a 15 ml centrifuge tube and the N-methylated products were back-extracted to 130 microliter of 0.1N acetic acid. After centrifugation, the organic layer was aspirated off and 100 microliter of the acetic acid phase was spotted on a silica gel plate with a multiple spotter. Thin layer chromatography was carried out in the chamber using as a developing solvent a mixture of tertiary amyl-alcohol, methylamine (40%), benzene (6:3:2, total 73.5 ml) for ninety minutes, in accordance with the procedure of Peuler and Johnson, supra. Then the plate was dried immediately. The metanephrine spot was marked under ultraviolet light, scraped off with a knife and transferred to a plastic vial containing 1 ml of 1N $NH_4OH$. Ten mls of ScintiVerse (obtained from the Fisher Scientific Co.) was added and the vial was left to stand for at least one hour prior to counting in a liquid scintillation counter. The plasma normetanephrine concentration was calculated from the radioactivity according to the formula given above.

Results

The mean recovery of normetanephrine in the deproteinization-concentration step was $87.6 \pm 1.3\%$ (mean $\pm$ SE, N=7) when tritiated normetanephrine (0.05 microCurie) was added to the pooled plasma. The overall mean recovery through the entire assay calculated when 1 ng of the levoform of normetanephrine was added to the pooled plasma was $70.0 \pm 2.8\%$.

The products of the incubated plasma yielded three peaks of radioactivity at the positions with Rf values of 0.34, 0.55 and 0.75 on the thin layer chromatography plate. The first two Rf values coincided with those of metanephrine and of synephrine. The radioactivity of the metanephrine position was relatively low in the normal plasma and separated clearly from the other peaks. Levo normetanephrine when added to pretreated plasma increased radioactivity only in the metanephrine spot. The radioactivity at the Rf value of 0.75 was not identified.

The intra- and inter-assay coefficient of variation of pooled plasma specimens were 7.5 and 8.2%, respectively. Table I lists normetanephrine excretion assayed in normal volunteers and in patients with pheochromocytoma, utilizing the above procedure. The results are expressed as mean $\pm$ the Standard Deviation.

TABLE I

Plasma Normetanephrine Concentrations in Supine
Normotensives and Patients with Pheochromocytoma

| Subjects | Age | Plasma Normetanephrine (pg/ml) |
|---|---|---|
| Normotensive | | |
| K. K. | 35 | 122 |
| M. L. | 30 | 44 |
| M. M. | 24 | 53 |
| R. M. | 35 | 94 |
| L. E. | 26 | 42 |
| S. J | 36 | 64 |
| S. O. | 32 | 86 |
| W. M. | 31 | 44 |
| G. N. | 33 | 31 |
| n = 9 | 31 ± 4 | 64 ± 30 |
| Pheochromocytoma | | |
| W. M. | 14 | 2100 |
| R. C. | 15 | 6150 |
| G. A. | 3 | 2630 |
| e = 3 | 11 ± 7 | 3630 ± 2200 |

As shown in Table I, patients with pheochromocytoma had values which were 30-fold, or more, greater than those of normotensives.

EXAMPLE II

Urine

PNMT was prepared as in Example I. Urine was collected for 24 hours, in bottles containing 15 ml of 6N HCl. To measure free normetanephrine the urine was diluted 1:10 with deionized water. Total normetanephrine was measured from hydrolyzed urine. The acid hydrolysis was performed by the addition of 0.4 ml of N HCl to 1 ml of urine followed by heating at 100° C. for 20 minutes. The hydrolyzed urine was then diluted 50 times with deionized water.

The assay procedure was conducted as described in Example I except that 10 microliters of urine were transferred to the culture tubes. Also 20 microliters of 0.001 NHCl were used for blanks rather than the 50 microliters of Example I.

EXAMPLES III and IV

Octopamine

The procedure of Examples I and II can be repeated but with the addition of 100 pg of octopamine in place of the 100 pg of normetanephrine as an internal standard, and by the addition of 5 micromole of unlabeled synephrine in place of the 5 micromole of metanephrine to facilitate chromatography band location. The pH of the incubation mixture is 9.3. The solvent system used is chloroform-ethanol-methylamine (40%) 16:3:2. In this case, synephrine bands are scraped into the scintillation vial and their counts per minute determined to yield the amount of octopamine, as synephrine.

EXAMPLES V AND VI

Brain Tissue

The procedure of Example I can be followed but in place of the urine sample one can use a sample of brain tissue.

EXAMPLE VII

Effect of pH

The procedure of Example II was repeated but using tris buffer containing 12.5 mM of EDTA from pH 7.5 to 9.5 for the radioenzyme assay at a final concentration of 60, 125 and 250 mM. As shown in FIG. 1, the optimal enzyme activity was found with 125 mM tris buffer between the pHs of 8.8 and 9.3.

Specificity of the Assay

Figure 2:
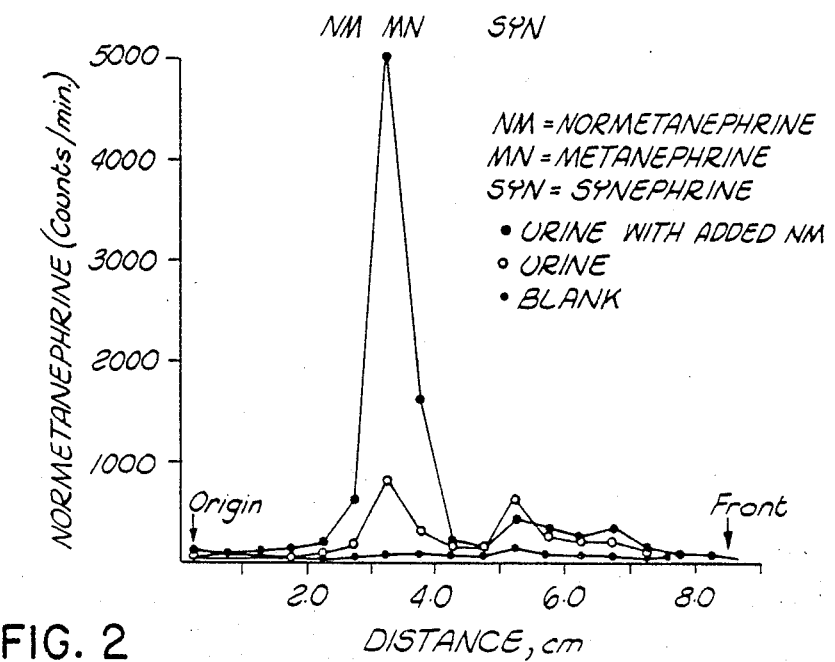
FIG. 2 is a plot of normetanephrine detected among other labeled products, versus the extent of chromatographic separation.

The conversions of normetanephrine to metanephrine and octopamine to synephrine were demonstrated after the separation of the reaction product on thin layer chromatography. As shown in FIG. 2, the blank did not show any obvious peak, whereas the sample and the sample with internal standard gave two distinctive peaks of radioactivity of the position metanephrine of (Rf 0.34) and synephrine (Rf 0.58). Most of the remaining radioactivity was diffused near the solvent front. A clear separation of metanephrine from synephrine was achieved, using t-amylalcohol-methylamine-benzene, 6:3:2.

EXAMPLE VIII

Substrate Specificity

To demonstrate the substrate specificity of the assay, the cross reactivities of catecholamines and their congeners were determined. Assays were conducted as in Example I using the solvent system of that example but in which the sample contained 250 pg of normetanephrine and in which there was added to the incubation mixture in individual tubes 10 microliters of the respective reagent listed in Table II. Thus, one tube referred to as the "blank" contained 250 pg of normetanephrine. Another tube contained 250 pg of normetanephrine and 10 microliters of a solution containing 500 pg of dopamine, norepinephrine, epinephrine, metanephrine, synephrine, tyramine or octopamine. Assays were also conducted with the blank and with each of the tubes containing reagent in the absence of the normetanephrine internal standard. After incubation and thin layer chromatography separation, as in Example I, the results shown in Table II were found, calculated using 250 pg in the formula rather than 100 pg.

TABLE II

Examination of the Effects of Phenolicamines and
Catechloamines on the Assay for Plasma Normetanephrine
Counts per Minute

| Amine | Sample | % | Normetanephrine Standard | Normetanephrine (pg) | Percentage Interference |
|---|---|---|---|---|---|
| Blank | 85 | 100 | 6141 | 0 | 0 |
| Dopamine | 80 | 1.3 | 6130 | 0 | 0 |
| Norepinephrine | 101 | 1.6 | 6020 | 0.6 | 0.1 |
| Epinephrine | 80 | 1.3 | 6124 | 0 | 0 |
| Metanephrine | 180 | 2.9 | 6363 | 3.8 | 0.7 |
| Synephrine | 262 | 4.2 | 6160 | 7.5 | 1.5 |
| Tyramine | 81 | 1.3 | 6090 | 0 | 0 |
| Octopamine | 726 | 11.8 | 7261 | 24.5 | 4.9 |

Referring to Table II, the cross reactivities of catecholamines and their congeners are seen to be negligible except for octopamine. However, octopamine would not interfere with the assay of normetanephrine on a clinical basis because the plasma concentration of octopamine is substantially lower than that of normetanephrine.

Linearity and Sensitivity

To determine the linearity of the assay, separate samples were prepared in which 5–100 pg of tritiated normetanephrine was dissolved in 10 microliters of distilled water. Each sample was added to 50 microliters of pretreated plasma and was assayed. Using the mean of two samples for each point, the linearity was observed in the range of 5-100 pg of tritiated normetanephrine. With urine, the linearity of the assay was examined with 1-normetanephrine added to both the distilled water and diluted urine. Excellent linearity was observed up to 500; the mean blank value obtained from a series of eleven assays shows 104±4 cpm (about 2.5 pg, n=11, mean±SD) and the content of normetanephrine in a sample corresponding to twice blank or equivalent to 5 pg of normetanephrine. This range of assay included the physiological range of metanephrine in humine urine which were 10-100 ng/ml of free normetanephrine and 50-300 ng/ml of total normetanephrine.

1-Normetanephrine is the preferred isomer as a substrate for PNMT and yielded about 1.5 times the activity of dl-normetanephrine. Thus, 1-normetanephrine should be used for calibration.

A linear relationship was shown when octopamine was added either to urine or to water at 3-500 pg. Similarly, a linear relation was observed when both the synephrine and dimethyloctopamine were counted together after thin layer chromatography. These findings indicate that methylation of synephrine is proportioned to the added amount of octopamine and therefore validates the measurement of octopamine with this assay. When the synephrine was recovered from thin layer chromatography, it yielded a lower blank and therefore increased sensitivity. The blank was found to be about 10% of sample without the thin layer chromatographic separation. An additional wash with borate buffer (pH 10) and the use of chloroform-ethanol-methylamine as developing solvents further reduced the blank to a mean value of 56±7 cpm (N=13). Two and one-half octopamine in urine yields about 120-140 cpm. One hundred pg of octopamine in urine yields 2,500-3,000 cpm. There was only 10% inhibition of the enzyme by the addition of 10 ul of diluted (1:10) urine.

Precision of the Assay

The intra and interassay coefficient variants (CV) were determined for the assay of normetanephrine. The sample which contained 53.7 ng of normetanephrine per ml of plasma gave an intraassay CV of 5.3% (N=7) and the interassay CV was found to be 6.8 (N=7). When the specimen contained only 14.1 ng of normetanephrine per ml of plasma the intraassay variable increased to 9.9% (N=7). Similar results were found for urinary octopamine. The intra and interassay CV were found to be 3.6% (N=11) and 5.8% (N=10), respectively.

The Accuracy of the Assay

The results of the radioenzymatic assay for normetanephrine were compared with those obtained by fluorometric method for the same samples; a linear relation was found between the results of the two methods.

We claim:

1. In a method for assaying a phenylethanolamine selected from normetanephrine and octopamine in a sample, in which method said phenylethanolamine is enzymatically transmethylated in an incubation mixture of said phenylethanolamine, a compound containing a transferable tritiated methyl group and a transfer enzyme, to form a tritiated N-methyl derivative, and the radioactivity of the derivative is measured, the improvement according to which incubation of said mixture is conducted at a pH in the range of 8.8-9.3.

2. The improvement of claim 1 including the steps, prior to incubation, of deproteinizing said sample and concentrating said phenylethanolamine.

3. The improvement of claim 1 in which said incubation mixture comprises a combination of tris and ethylenediaminetetraacetic acid.

4. The improvement of claim 2 in which said sample is deproteinized by reacting protein therein with trichloroacetic acid and separating the reaction product from said sample.

5. The improvement of claim 2 or 4 in which the phenylethanolamine in said sample is concentrated by weak cation exchange.

6. The improvement of claim 5 in which said weak cation exchange is conducted by chromatographic extraction through weak cation exchange resin.

7. In a method for assaying normetanephrine in a sample, in which method said normetanephrine is enzymatically transmethylated in an incubation mixture of said normetanephrine, S-adenosyl-L-methionine having a transferable tritiated methyl group and phenylethanolamine-N-methyl transferase, to form tritiated metanephrine, and the radioactivity of the tritiated metanephrine is measured, the improvement according to which said incubation mixture is a combination of tris and ethylenediaminetetraacetic acid having a pH in the range of 8.8-9.3 and including the steps, prior to incubation, of deproteinizing said sample by reacting protein therein with trichloroacetic acid, separating the reaction product of said sample and concentrating the phenylethanolamine of said sample by chromatographic extraction through weak cation exchange resin.

8. In a method for assaying octopamine in a sample in which method said octopamine is enzymatically transmethylated in an incubation mixture of said octopamine, a compound containing a transferable tritiated methyl group and a transfer enzyme, to form tritiated synephrine, and the radioactivity of the tritiated synephrine is measured, the improvement according to which said incubation mixture is in the range of 8.8-9.3.

9. The improvement of claim 8 including the steps, prior to incubation, of deproteinizing said sample and concentrating said octopamine.

10. The improvement of any one of claims 1, 7 and 8 in which said sample comprises urine.

11. The improvement of any one of claims 1, 7, 8 and 9 in which said sample comprises plasma.

12. The improvement of any one of claims 1, 7, 8 and 9 in which said sample comprises brain tissue.

* * * * *